United States Patent [19]

Ender

[11] Patent Number: 5,084,053
[45] Date of Patent: Jan. 28, 1992

[54] BONE NAIL AND TOOL FOR THE CONNECTION TO THE DISTAL END AREA OF SUCH A BONE NAIL

[76] Inventor: Hans G. Ender, Krenngasse 3, Vienna, Austria, A-1180

[21] Appl. No.: 602,692

[22] Filed: Oct. 24, 1990

[30] Foreign Application Priority Data

Oct. 25, 1989 [AT] Austria ................... 2463/89

[51] Int. Cl.⁵ ............................................. A61B 17/58
[52] U.S. Cl. ..................................... 606/104; 606/62; 606/67; 403/341
[58] Field of Search .............. 606/104, 60, 62-64, 606/67; 433/3; 403/339-341

[56] References Cited

U.S. PATENT DOCUMENTS

| 986,761 | 3/1911 | Roscoe | 403/341 X |
|---|---|---|---|
| 1,975,244 | 10/1934 | Wiseman | 403/339 X |
| 4,055,172 | 10/1977 | Ender et al. | 606/62 |
| 4,169,470 | 10/1979 | Ender et al. | 606/62 |
| 4,467,793 | 8/1984 | Ender | 606/62 |
| 4,630,601 | 12/1986 | Harder et al. | 606/62 |
| 4,817,591 | 4/1989 | Klaue | 606/64 |

FOREIGN PATENT DOCUMENTS

| 2527460 | 1/1976 | Fed. Rep. of Germany | 606/62 |
|---|---|---|---|
| 2535697 | 2/1977 | Fed. Rep. of Germany | 606/62 |
| 466232 | 5/1937 | United Kingdom | 403/341 |

OTHER PUBLICATIONS

Richards Manf. Co., Hanson-Street Nail and Extraction Starter, 1949.

Primary Examiner—Robert A. Hafer
Assistant Examiner—Kevin G. Rooney
Attorney, Agent, or Firm—Fleit, Jacobson, Cohn, Price, Holman & Stern

[57] ABSTRACT

A bone nail of elastic material bent at least in its proximal end portion and insertable into the medullary canal of the bone through an impact hole formed proximal to the knee joint area of the bone has the same cross section in its distal end area as the entire nail and is provided with a flattening for forming a coupling element for the non-rotatable connection with the tool in at least one site of the nail periphery at a distance from the distal nail end, with at least the front face immediately adjacent the distal nail end via which the flattening merges with the periphery of the bone nail, preferably both opposing front faces, extending inclined to the flattening, and thus form an angle deviating from 90 degrees, peferably an angle of about 45 degrees, with said flattening.

19 Claims, 2 Drawing Sheets

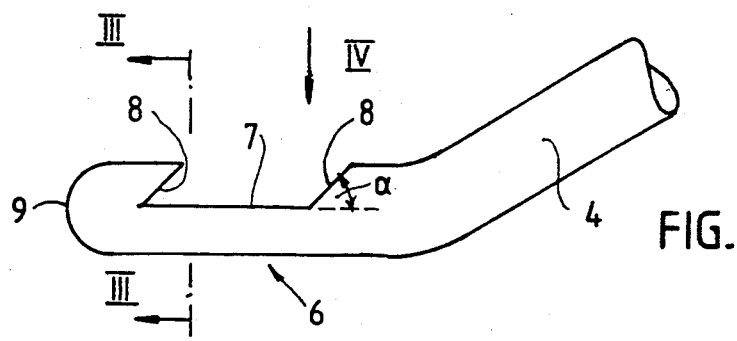
FIG. 2

FIG. 4
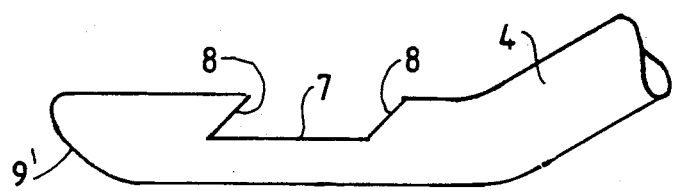
FIG. 5
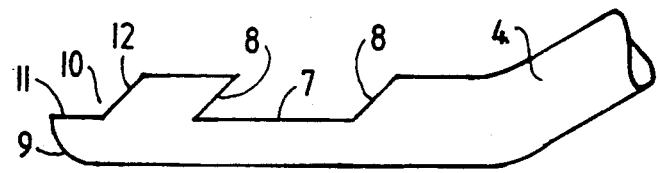
FIG. 6

FIG. 7

FIG. 9
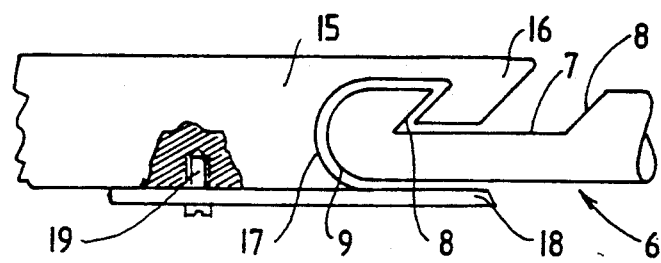
FIG. 11

BONE NAIL AND TOOL FOR THE CONNECTION TO THE DISTAL END AREA OF SUCH A BONE NAIL

BACKGROUND OF THE INVENTION

1. Field of the Invention

The invention relates to a bone nail bent at least in its proximal end portion and consisting of elastic material of round or oval cross section for fixing fractures in the proximal femural area, comprising at least one bone nail of resilient material, which nail is insertable into a medullary canal of a bone through an impact hole formed in the bone proximal to the knee joint area and which abuts under tension with its apex of curvature the wall of the medullary canal opposing the impact hole due to its elasticity, whose portion adjacent the distal end of the bone nail has the same cross section as the entire nail, and which is provided for forming as a coupling element for the production of a non-rotatable connection to a tool with a flattening in at least one site of the nail circumference at a distance from the distal nail end. The invention further relates to a tool for the connection to the distal end area of such a bone nail.

2. Discussion of the Prior Art

It is known to reposite and to fix pertrochanterous and subtrochanterous fractures by opening the medullary canal of the bone through an impact hole and by introducing into this impact hole at least one bone nail, conveniently several bone nails consisting of elastic material and being bent at least in its (their) proximal area. When introducing such bone nails into the medullary canal, the nails, under tension due to their elasticity, abut the wall of the medullary canal opposing the impact hole with their apex of curvature, so that on the proximal point of each nail arriving at the site of the fracture, the nail passes beyond this fracture into the condyle of the bone and fixes the fracture. By rotating the individual nails, the bone portions can be reduced so that they assume the correct relative position at the site of the fracture. For this purpose, the distal end of each nail is provided with a coupling member allowing a wholly non-rotatable connection with an impact tool.

It is known to give this coupling member the form of a hook-shaped bend. The drawback of this known embodiment resides in the fact that the hook-shaped bends protrude far out, the sinews and muscles are irritated and the bending of the leg is impeded in the area of the knee joint. Moreover, when using several bone nails, such as this is done as a rule, these hook-shaped bends impede one another. And finally, the hook-shaped bends, due to the elastic bone nails placed in the bone under tension, bear on a comparatively small site of the outer surface of the bone with considerable force, so that in particular in the case of older people with porous bones, there is the hazard of the bone caving in at this site.

It has been proposed to form the coupling part as a platelet-shaped flattening of the distal nail end. In this embodiment, the coupling part requires less space, the individual platelet-like flattenings can superimpose in the manner of roof tiles and do not hamper each other and the specific pressure per unit area is reduced by increasing the area, so that the hazard of the bone caving in in the area of the flat platelets abutting the outer surface of the bone is reduced, but not completely eliminated. Moreover, these platelets protruding from the impact hole also irritate the sinews and muscles running over this impact hole.

Further known is a bone nail of elastic material bent at least in its proximal end portion whose distal end portion has the same cross section as the entire nail and is provided with a flattening on at least one site of the nail periphery at a distance from the distal nail end, whereby this end area is formed as a coupling element permitting a non-rotatable connection to a tool serving for driving the nail. In this embodiment, the distal end area thus has no larger dimensions and still allows for the forming of a non-rotatable connection to the said tool for driving the nail. The distal nail ends can thus be accommodated in the guiding channel of a known insert member fixed in the impact hole of the bone whose guiding channel can have small dimensions because the distal end portions of the nails are not enlarged. An insert member of this type prevents the impact hole from splintering in the bone on driving the nail and thus becoming unintentionally enlarged and further permits the accommodation of the distal nail ends in the guiding channel so that they no longer protrude from the bone. This prevents an irritation of the muscles and sinews and the caving in of the bone in the area of the impact hole because the distal end of the nails formed as a coupling element no longer abuts the outer surface of the bone under tension, but instead the forces are taken up by the insert member and distributed by this evenly along the entire periphery of the impact hole to the bone.

In the known bone nails having at least one flattening at the distal nail end, the front faces via which the flattening merges with the circumference of the bone nail extend perpendicularly to the flattening. As a result, in this known embodiment, those parts of the tool cooperating with the flattening must be fixed by means of a sleeve in order to prevent slipping off from the flattening. This sleeve considerably increases the circumference of the tool in that area where the coupling of the same with the distal nail end formed as a coupling element takes place. When the distal nail ends are accommodated in the guiding channel of the said insert member having small dimensions, the coupling of the tool with the distal nail ends is difficult and sometimes impossible for lack of space. This constitutes a major disadvantage particularly when driving the nails back for removal from the medullary canal. For while the nail can be driven into the medullary canal during the last step of driving in which the distal nail ends enter the guiding channel by means of a tool which cooperates merely with the nail end on the front side, which no longer requires a coupling by means of the flattening, the driving back of the bone nails for removing them from the medullary canal demands a connection between the nail and the tool required for the driving back via the flattening.

SUMMARY OF THE INVENTION

It is the object of the invention to improve a bone nail of the type initially described in such a manner that a connection of the portion adjacent the distal nail end with a tool whose dimensions at the site of connection can be kept small and by means of which a removal of the nails from the medullary canal is also possible can be established.

It is a further object of the invention to improve a bone nail of the type initially described in such a manner that the connection of the portion adjacent the distal nail end with the tool in a non-rotatable manner can be achieved without additional measures and still without increasing the dimensions of this portion.

It is a further object of the invention to form the bone nail in such a manner that unreasonable stress at the connection site between the bone nail and the tool can be prevented on driving in, removing and rotating of the bone nail.

It is a further object of the invention to form the bone nail in such a manner that it may shift distally after insertion into the medullary canal so as to prevent a perforation of the condyle by the point of the proximal nail end on subjecting the leg to stress which causes the fragments at the fraction site to approach. This is to prevent jamming of the portion of the bone nail adjacent the distal nail end, as this jamming would prevent the sliding of the bone nail.

It is a further object of the invention to form a tool for the connection to the bone nail in such a manner that a slipping off of the tool from the bone nail on pulling the bone nail out of the medullary canal is prevented.

It is a further object of the invention to form this tool in such a manner that the bone nail can be safely inserted into the medullary canal by means of this tool.

BRIEF DESCRIPTION OF THE DRAWINGS

In the drawings, the embodiments of the invention are schematically illustrated.

FIG. 2 shows the distal end area of a bone nail according to the invention in elevational view at enlarged scale;

FIGS. 5 to 7 and 9 show modified embodiments of the distal end area of a bone nail according to the invention in elevational view corresponding to the representation in FIG. 2;

FIG. 11 represents a portion of the tool according to the invention in cooperation with the distal end area of a bone nail according to the invention.

DESCRIPTION OF THE PREFERRED EMBODIMENTS

Figure 1:
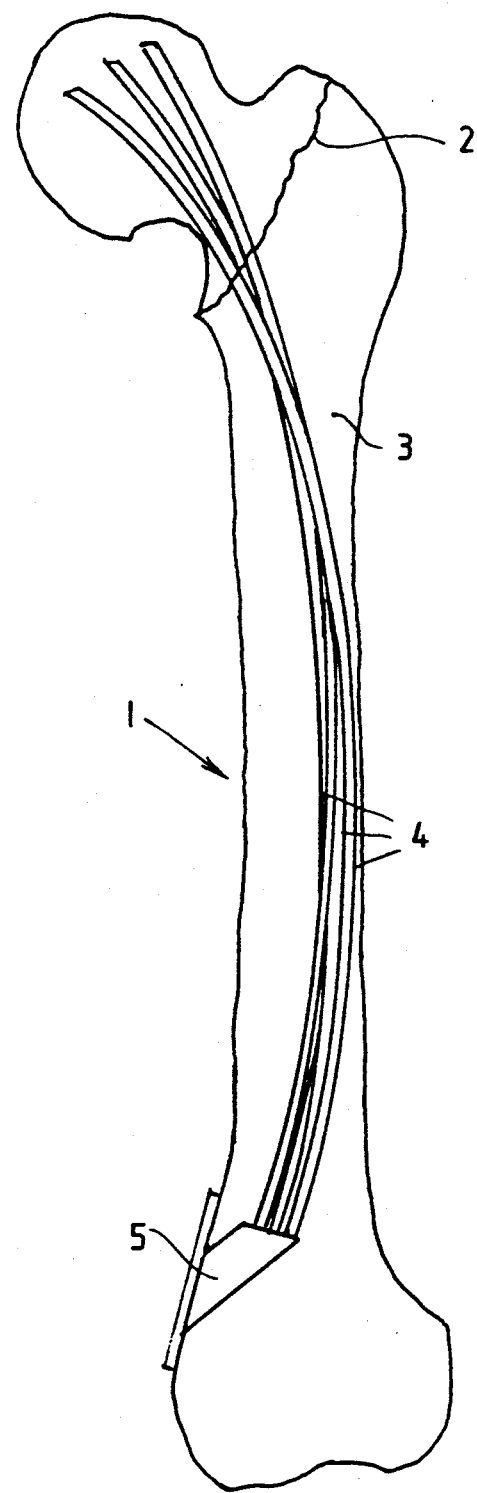
FIG. 1 shows a bone having a fracture provided with three bone nails according to the invention.

FIG. 1 shows a bone 1 having a fracture 2. For repositioning and fixing the fracture 2, three bone nails 4 consisting of elastic material of round cross section and bent in their proximal end portion are inserted into the medullary canal 3 of the bone 1. To this end, the medullary canal is opened by puncturing at the joint portion of the bone and an impact hole is then milled or bored by means of a milling cutter or a drill, the axis of the hole being so selected that the nails 4 can be driven in the required direction. Subsequently, an insert member 5 is inserted into the impact hole, then the bone nails are driven in and rotated for reducing and fixing the fracture site. For this purpose, the bone nails are provided at their respective distal end areas 6 with a coupling member shown in detail in FIGS. 2 to 10.

As shown in FIGS. 2 to 10, the distal end area 6 has the same cross section as the remaining bone nail 4 and is recessed to provide a flattening (base surface) 7 merging with the periphery of the bone nail via front and back faces 8. The front and back faces 8 are mutually parallel and extend inclined to the flattening 7, preferably forming an angle of between 30 and 60 degrees, in particular of 45 degrees, with the flattening 7. The inclination of the front faces is so selected that they extend starting from the circumference of the bone nail to the flattening 7 in the direction towards the distal nail end 9.

By the configuration of the faces 8 according to the invention, as explained in detail in the following in connection with FIG. 11, a secure connection with the portion of a tool cooperating with the flattening 7 is assured without additional measures for fixing this tool portion being required. For the inclined formation of this front face 8 prevents the portion of the tool cooperating with the flattening from sliding off the flattening 7 on driving the bone nail 4 in and particularly on removing it by means of this tool and thus becoming released from the bone nail 4 even if no additional measures for fixing this portion of the tool are provided. The embodiment according to the invention thus permits a coupling between the distal nail ends accommodated in the guiding channel of an insert member 5 and a suitable tool for the purpose of removing the nails form the medullary canal even if several nails 4 are arranged in the medullary canal 3 and the dimensions of the guiding channel are small so that there is little space for introducing the tool into the guiding channel of the insert member 5 available.

Figure 3:
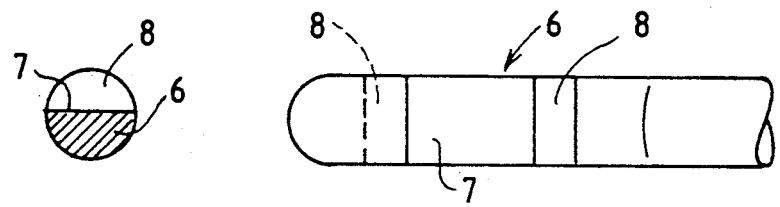
FIG. 3 is a sectional view along line III—III in FIG. 2 and FIG. 4 a plan view in the direction of arrow IV in FIG. 2.

In the embodiment according to FIGS. 2 to 4, the distal nail end 9 is formed as a spherical segment.

FIG. 5 shows an embodiment in which the distal nail end 9' is defined by a curve in cross section extending inclined to the flattening 7 in a normal plane coinciding with the paper plane and extending in longitudinal direction of the nail, the inclination of this curve being opposed to the inclination of the front face 8 adjacent the distal nail end. This embodiment allows an unhindered sliding of the distal nail end 9' along the wall of the guiding channel of an insert member which is required on loading a leg in whose medullary canal the nails are inserted, in order to prevent that the condyle becomes perforated by the tip of the proximal nail end when the fragments are shoved together on loading the fractured leg.

FIG. 6 shows an embodiment in which the distal nail end 9 is shaped as a spherical segment, although with a recess 10 indented in the circumferential surface of the nail and open towards the distal nail end 9. The boundary surface 11 of the recess 10 extends parallel to the flattening 7 and merges via an inclined surface 12 extending parallel to the front face 8 with the peripheral surface of the bone nail. By this configuration, a secure non-rotatable connection of the nail and an appropriately formed tool such as it is necessary on reducing the fracture site by rotating the nail is assured.

Figure 8:
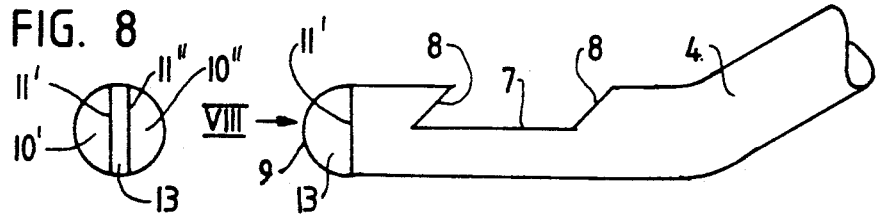
FIG. 8 shows a front view of the distal end area of the bone nail shown in FIG. 7 in the direction of arrow VIII in FIG. 7

FIGS. 7 and 8 show an embodiment in which two recesses 10', 10" open towards the nail end and indented from two opposing peripheral surfaces define a projection 13 directed to the distal nail end. This projection, by cooperating with an appropriately formed tool, also assures an additional non-rotatable connection between this tool and the bone nail. In the embodiment according to FIGS. 7 and 8, the boundary surfaces 11', 11" of the two recesses 10', 10" extend perpendicularly to the flattening 7.

Figure 10:
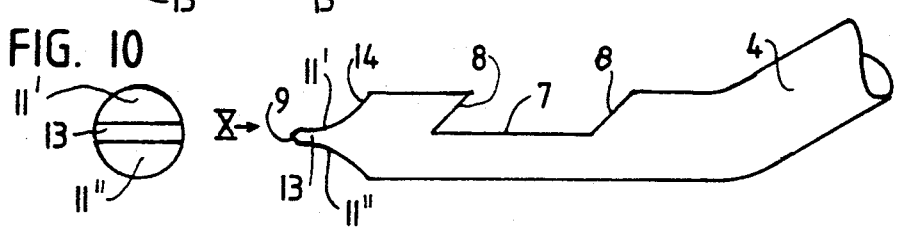
FIG. 10 shows a front view of the distal end area of the bone nail represented in FIG. 9 in the direction of arrow X in FIG. 9.

The embodiment according to FIGS. 9 and 10 differs from the embodiment according to FIGS. 7 and 8 in that the boundary surfaces 11', 11" in this case extend parallel to the flattening 7. Moreover, according to this embodiment, the boundary surfaces 11', 11" merge with the peripheral surface of the bone nail via an inclined surface 14.

In FIGS. 2 to 10, merely one single flattening 7 with inclined front face 8 is represented. A single flattening like this is sufficient for the coupling of the distal end area of the bone nail with an appropriately formed tool. In some cases, however, it may prove convenient to have this tool suitable for coupling with the distal end area of the bone nail in several locations. For this purpose, several flattenings 7 with inclined front faces 8 can be provided in the distal end area, offset not only in peripheral direction, but also in longitudinal direction of the nail.

FIG. 11 shows the portion of a tool 15 cooperating with the distal end area 6 on a bone nail. This tool is provided with a hook-shaped projection 16 adapted to the shape of the front face 8 via which the flattening 7 merges with the peripheral face of the nail, projection 16 gripping said front face 8 from behind, and merges via a curved surface 17 adapted to the shape of the distal nail end 9 with the shaft of the tool. The distal end area between the front face 8 and the nail end 9 is thus enclosed by the said parts of the tool. Such a tool can be used for driving the bone nail into the medullary canal and also for driving the bone nail out of the medullary canal and requires little space so that it can also be coupled with the distal end area of the bone nail if this is located within the guiding channel of an insert member. In order to prevent the release of the tool from the portion adjacent the distal nail end with certainty, the shaft of the tool is provided on the side diametrically opposed to the hook-shaped projection 16 with a resiliently formed tongue 18, for instance of spring steel, connected to the tool shaft via a screw 19. This resiliently formed tongue springs out during the coupling operation of the tool with the distal end area of the bone and thus does not impede this coupling operation, but instead abuts the peripheral surface of the bone nail as soon as the hook-shaped projection 16 has gripped around the front face 8. As the resiliently formed tongue 18 can be comparatively thin, it only negligibly increases the dimensions of the tool.

What is claimed is:

1. A bone nail of elastic material for fixing fractures in the proximal femural area, which nail is insertable via an impact hole proximal to a knee joint area of a bone into a medullary canal of the bone and suitable for abutting under tension due to its elasticity a wall of the medullary canal opposite the impact hole with an apex of curvature, a portion of the nail adjacent a distal nail end has a cross section corresponding to that of the entire nail and is recessed to provide a base surface and front and back faces for forming a coupling element for non-rotatable connection with a tool, at least the front face which is adjacent the distal nail end being inclined and starting from the base surface extending outwardly and away from the distal nail end, so that said front face forms an undercut angle deviating from 90 degrees with said base surface.

2. The bone nail according to claim 1, wherein the back face is inclined and extends outwardly from the base surface away from the distal nail end.

3. The bone nail according to claim 2, wherein the front and back faces are parallel to one another.

4. The bone nail according to claim 1, wherein the angle which the inclined front face forms with the base surface is an angle of 30 to 60 degrees.

5. The bone nail according to claim 4, wherein the angle which the inclined front face forms with the base surface is an angle of approximately 45 degrees.

6. The bone nail according to claim 1, wherein the nail is recessed to provide at least two base surfaces with front and back faces offset in a peripheral direction of the nail.

7. The bone nail according to claim 1, wherein at least two flattenings offset in the longitudinal direction of the nail are provided.

8. The bone nail according to claim 1, wherein the distal nail end is provided with at least one recess indented from a peripheral surface of the nail and open towards the end of the nail.

9. The bone nail according to claim 8, including recesses defining a projection directed towards the distal nail end provided on two diametrically opposed peripheral surfaces of the nail.

10. The bone nail according to claim 8, wherein the recess has a boundary surface which extends at least partially parallel to said base surface.

11. The bone nail according to claim 8, wherein the recess has a boundary surface which extends at least partially perpendicularly to the base surface.

12. The bone nail according to claim 8, wherein the recess has a boundary surface which merges with a peripheral surface of the nail in a curve.

13. The bone nail according to claim 8, wherein the recess has a boundary surface which merges with a peripheral surface of the nail via an inclined surface.

14. The bone nail according to claim 13; wherein the inclined surface has an inclination equal to the inclination of the inclined front face.

15. The bone nail according to claim 1, wheren the distal nail end is in cross section defined by a curve inclined to the base surface in a plane normal to the base surface extending in longitudinal direction of the nail.

16. The bone nail according to claim 15, wherein the curve has an inclination opposite of the inclination of the front face.

17. A bone nail according to claim 1, in combination with a tool having a tool shaft provided with a hook-shaped projection adapted to engage with said front face.

18. The combination accordintg to claim 17, wherein the hook-shaped projection merges with the tool shaft via a curved surface adapted to the form of the distal nail end.

19. The combination to claim 17, wherein the tool shaft is provided with a resiliently formed tongue diametrically opposed to the hook-shaped projection.

* * * * *